United States Patent [19]
Shimizu et al.

[11] Patent Number: 6,030,640
[45] Date of Patent: Feb. 29, 2000

[54] OLIGOGLYCINE COMPOUND, FIBROUS MICROTUBE OF OLIGOGLYCINE COMPOUND AND PROCESS OF PRODUCING FIBROUS MICROTUBE

[75] Inventors: Toshimi Shimizu; Masaki Kogiso, both of Tsukuba; Mitsutoshi Masuda, Matsudo, all of Japan

[73] Assignee: Director-General of Agency of Industrial Science and Technology, Japan

[21] Appl. No.: 09/184,631

[22] Filed: Nov. 3, 1998

Related U.S. Application Data

[62] Division of application No. 08/916,375, Aug. 22, 1997, Pat. No. 5,876,748.

[30] Foreign Application Priority Data

Aug. 29, 1996 [JP] Japan ................................. 8-227974

[51] Int. Cl.⁷ ...................... C07C 233/04; C08G 69/10; C08G 69/26
[52] U.S. Cl. .......................... 424/450; 424/460; 424/477; 424/499; 514/17; 514/18; 514/19; 436/71
[58] Field of Search ..................... 424/450, 460, 424/477, 499; 514/17, 18, 19; 436/71

[56] References Cited

U.S. PATENT DOCUMENTS

| | | | |
|---|---|---|---|
| 4,638,045 | 1/1987 | Kohn et al. | 530/323 |
| 4,990,291 | 2/1991 | Schoen et al. | 264/4.7 |
| 5,101,011 | 3/1992 | Mikami et al. | 528/328 |

*Primary Examiner*—Nathan M. Nutter
*Attorney, Agent, or Firm*—Lorusso & Loud

[57] ABSTRACT

A lipid represented by the following formula:

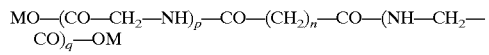

wherein M represents a hydrogen atom or an alkali metal, n is an integer of 6–18 and p and q each represent an integer of at least 1 with the proviso that a total of p and q is not greater than 6. When an aqueous solution of an alkali metal salt of the lipid is allowed to stand for 2–3 weeks, a fibrous microtube including a tubular body having a diameter of 1–3 $\mu$m and a plurality of spherical vesicles contained within the tubular body and having a diameter of 0.1–3 $\mu$m is formed.

3 Claims, 2 Drawing Sheets

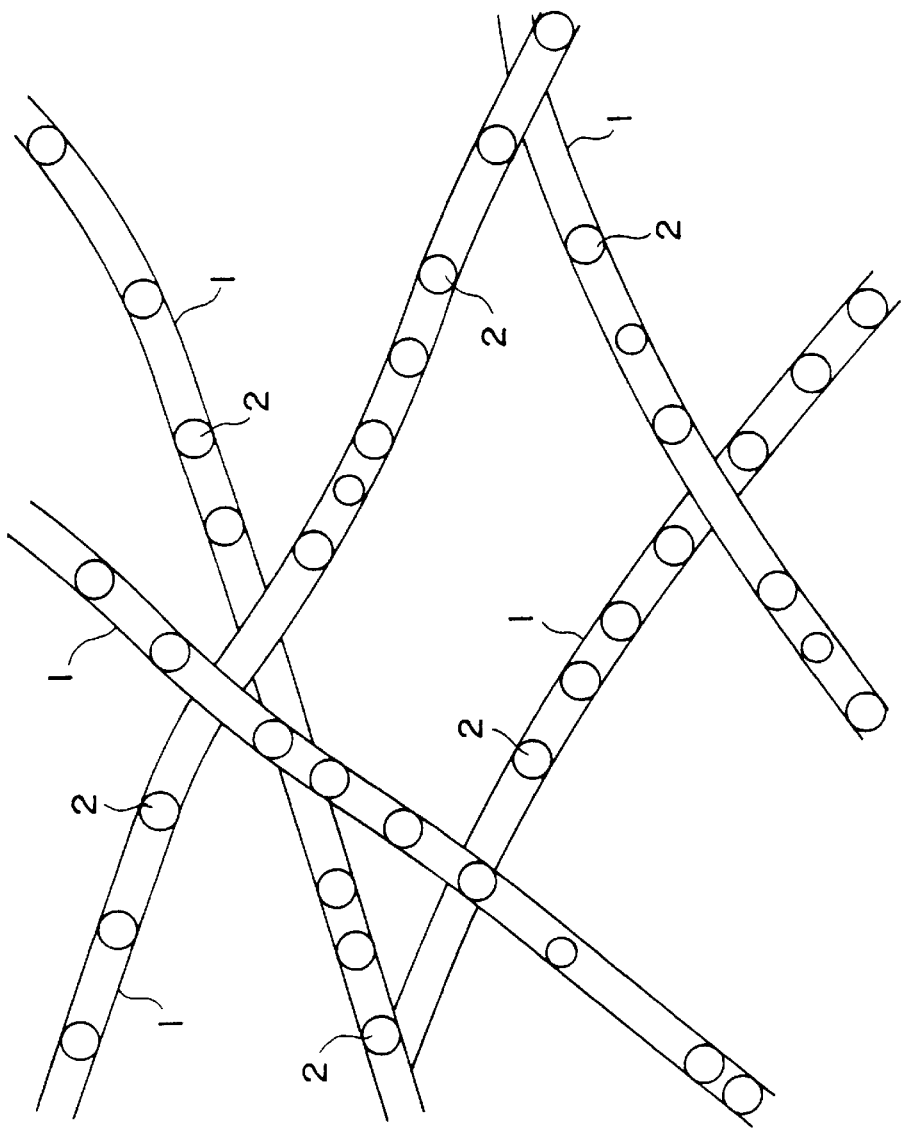

OLIGOGLYCINE COMPOUND, FIBROUS MICROTUBE OF OLIGOGLYCINE COMPOUND AND PROCESS OF PRODUCING FIBROUS MICROTUBE

CROSS-REFERENCE TO RELATED APPLICATION:

This application is a division of U.S. Ser. No. 08/916,375 filed August 22, 1997, and now U.S. Pat. No. 5,876,748.

BACKGROUND OF THE INVENTION

This invention relates to a novel peptide lipid of an oligoglycine compound, to a fibrous microtube made of the peptide lipid and a process of producing the fibrous microtube.

Liposomes made of a phospholipid are known. These liposomes are in the form of spheres having a single-wall or multi-wall structure and a diameter of 0.02–1 µm. Also known is a giant vesicle having a diameter of 5–10 µm and containing a plurality of small spherical aggregates (Angewandte Chemie International Edition of English, vol. 34, 2091–2106 (1995)). The giant vesicle is prepared by dispersing a synthetic compound, such as didodecyldimethylammonium bromide, having both hydrophilic and hydrophobic groups in water and is stable only in the presence of water.

SUMMARY OF THE INVENTION

It is an object of the present invention to provide a novel peptide lipid which is useful for forming molecular assemblies in the form of microtubes.

Another object of the present invention is to provide molecular assemblies in the form of fibrous microtubes which have a larger inside volume in comparison with the known vesicles and which can contain a large volume of an aqueous solution.

It is a further object of the present invention to provide molecular assemblies of the above-mentioned type which are stable in a dried state.

It is yet a further object of the present invention to provide a simple method for the preparation of the above fibrous molecular assemblies.

In accordance with one aspect of the present invention there is provided a lipid represented by the following formula:

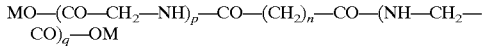

wherein M represents a hydrogen atom or an alkali metal, n is an integer of 6–18 and p and q each represent an integer of at least 1 with the proviso that a total of p and q is not greater than 6.

In another aspect, the present invention provides a fibrous microtube comprising a tubular body and a plurality of spherical vesicles contained within said tubular body, each of said tubular body and said vesicles being a lipid represented by the following formula:

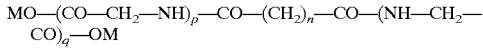

wherein M represents an alkali metal, n is an integer of 6–18 and p and q each represent an integer of at least 1 with the proviso that a total of p and q is not greater than 6.

The present invention also provides a process for the preparation of a fibrous microtube comprising a tubular body and a plurality of spherical vesicles contained within said tubular body, each of said tubular body and said vesicles being a lipid represented by the following formula:

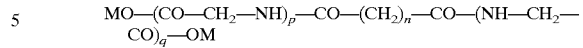

wherein M represents an alkali metal, n is an integer of 6–18 and p and q each represent an integer of at least 1 with the proviso that a total of p and q is not greater than 6, said process comprising the step of allowing an aqueous solution of said lipid to stand in air or in an atmosphere of an organic acid for a period of time sufficient to grow said fibrous microtube.

BRIEF DESCRIPTION OF THE DRAWINGS

Other objects, features and advantages of the present invention will become apparent from the detailed description of the preferred embodiments of the invention which follows, when considered in light of the accompanying drawings in which:

FIG. 2 is a schematic illustration of an example of a fibrous microtube according to the present invention.

DETAILED DESCRIPTION OF THE PREFERRED EMBODIMENTS OF THE INVENTION

Figure 1:
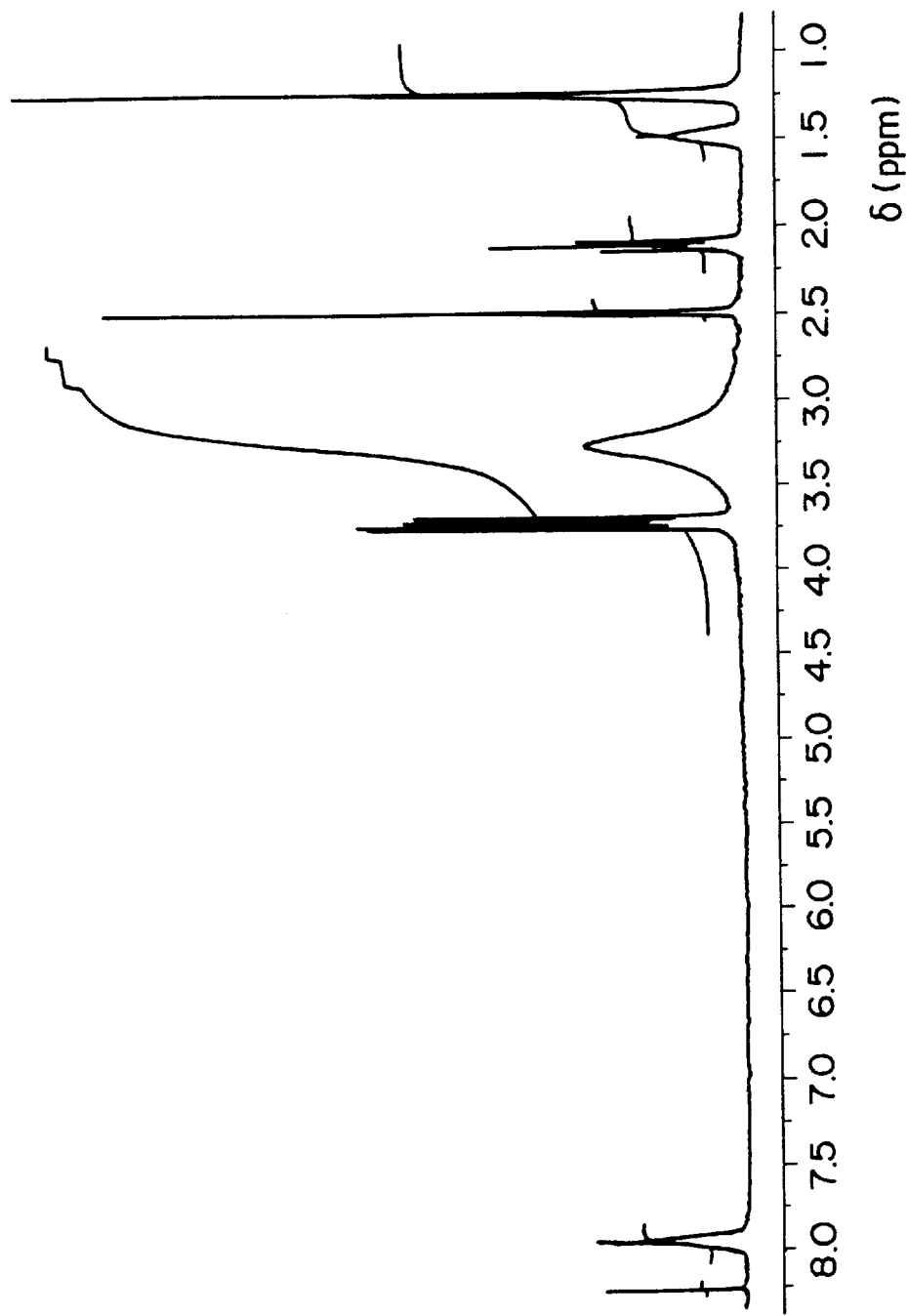
FIG. 1 is a proton NMR chart of N,N'-bis(glycylglycine) decane-1,10-dicarboxyamide which is one of the novel oligoglycine compounds according to the present invention.

A novel peptide lipid according to the presently invention is a oligoglycine compound represented by the following formula (I):

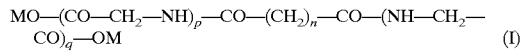

wherein M represents a hydrogen atom or an alkali metal, n is an integer of 6–18 and p and q each represent an integer of at least 1 with the proviso that a total of p and q is not greater than 6. M is preferably a hydrogen atom, sodium, potassium or lithium. The peptide lipid is useful for preparing fibrous microtubes as described hereinafter.

When the total number of p and q is greater than 6, the peptide lipid is insoluble in water so that it is difficult to use the peptide lipid for the preparation of fibrous microtube assemblies. For reasons of easiness in preparation of the peptide lipid, it is preferred that p and q be the same and be in the range of 1 to 3. When n is smaller than 6, it is difficult to use the peptide lipid for the preparation of fibrous microtubes. Too large a number of n in excess of 18 is also disadvantageous, because the peptide lipid gives amorphous solids and cannot form fibrous microtubes. The number n is preferably 6–12. Illustrative of suitable —$(CH_2)_n$— groups are hexylene, octylene, nonylene, decylene, undecylene, dodecylene, tetradecylene, hexadecylene and octadecylene.

The novel peptide lipid of the formula (I) may be prepared by reacting an oligoglycine hydrochloride of the formula (II):

wherein R is a protective group and r is an integer corresponding to p and q defined above, with a dicarboxylic acid of the formula (III):

wherein n is as defined above. The product obtained by the above reaction (condensation) is thereafter treated to remove the protective group. The resulting peptide lipid which is a white solid at room temperature may be purified by washing with an acid or alkali and by recrystallization.

The protective group R may be, for example, methyl, ethyl, benzyl, p-nitrobenzyl, p-methoxybenzyl or t-butyl. The oligoglycine hydrochloride of the formula (II) may be obtained by any suitable known method. For example, $HCl\cdot H—(NH—CH_2—CO)_3—OCH_2C6H_5$ may be produced by a method including the steps of (a) reacting a N-protected glycine with a C-protected glycine (glycine benzyl ester) to obtain a dipeptide, (b) removing the protective group of N-terminus, (c) then reacting the resulting dipeptide with N-protected glycine to obtain a tripeptide, and (d) then removing the protective group of N-terminus. Any protective group R for the carboxyl group, protective group for the amino group and coupling agent conventionally employed in the synthesis of oligopeptides may be suitably used for the purpose of the preparation of the oligoglycine hydrochloride of the formula (II). The intermediate peptides and the final oligoglycine product may be purified by washing with an acid or alkali and by recrystallization, if desired.

Examples of the dicarboxylic acid of the formula (III) are suberic acid, azelaic acid, sebacic acid, 1,9-nonanedicarboxylic acid, 1,10-decanedicarboxylic acid, 1,11-undecanedicarboxylic acid, 1,12-dodecanedicarboxylic acid, 1,13-tridecanedicarboxylic acid, 1,14-tetradecanedicarboxylic acid, 1,16-hexadecanedicarboxylic acid and 1,18-octadecanedicarboxylic acid.

The above peptide lipid of the formula (I) is suitably used for the fabrication of a fibrous microtube according to the present invention as schematically shown in FIG. 1. The fibrous microtube includes a tubular body 1 and a plurality of spherical vesicles 2 encapsulated in the tubular body 1.

The tubular body 1 generally has a diameter of about 1–3 µm and a length in the range of 200 µm to 5 mm and is formed from a thin wall (generall 10–100 nm thick) of the peptide lipid of the formula 1. Each of the spherical vesicles has a diameter of about 0.1–3 µm and is formed from a thin wall (generally 10–100 nm thick) of the peptide lipid of the formula 1. The tubular body 1 may be linear or branched. The tubular body 1 is closed at termini thereof or is open at least one terminus thereof. Each of the tubular body 1 and the spherical vesicles is filled with an aqueous liquid.

The fibrous microtubes may be obtained by allowing an aqueous solution of an alkali metal salt of the peptide lipid of the formula (I) to stand, preferably quiescently, in air or in an atmosphere of an organic acid for a period of time sufficient to grow the fibrous microtube, preferably from 3 days to 4 weeks.

The aqueous solution of an alkali metal salt of the peptide lipid may be obtained by dissolving the peptide lipid of the formula (I) in which M is the alkali metal in water. Alternatively, the peptide lipid of the formula (I) in which M is hydrogen is dissolved in an aqueous alkali metal solution containing approximately twice equivalent of the alkali metal to obtain the aqueous solution of an alkali metal salt of the peptide lipid. The aqueous solution of the alkali metal salt of the peptide lipid preferably has a lipid concentration of 5 mM to 15 mM. Too high a concentration above the saturated point is undesirable because an amorphous solid is apt to be produced. When the lipid concentration is excessively low, a long period of time is required for the formation of molecular assemblies in the form of fibrous microtubes.

The formation and growth of the microtubes is generally performed at a temperature of 5–40° C. The organic acid atmosphere may be, for example, an atmosphere of formic acid, acetic acid, propionic acid, butyric acid or valeric acid. The atmosphere of the saturated vapor pressure of a 0.2–2% by weight aqueous organic acid solution may be suitably used.

The fibrous microtubes of the peptide lipid as obtained have a structure in which the tubular body 1 (FIG. 1) is closed at its termini. When the as obtained fibrous microtubes are isolated by, for example, decantation, and dehydrated and dried under vacuum, there are obtained fibrous microtubes which are stable in air. When the dried fibrous microtubes is immersed in water and sonicated, there are obtained fibrous microtubes in which each of the tubular bodies 1 is open at at least one terminus thereof.

The open ended fibrous microtubes may be utilized, for example, as releasing containers for a water-soluble medicine (medicine is gradually released from the tubes), capillary tubes and artificial blood tubes. Closed fibrous microtubes may be utilized, for example, containers for a water-soluble medicine, containers for solid micro particles (e.g. catalyst metal particles) and containers for the growth of microorganisms. The medicine and microparticles may be incorporated into the tubular body and spherical vesicles during the growth of the fibrous microtubes. Alternatively, an aqueous solution of a medicine having any desired concentration may be injected into the tubular body and/or spherical vesicles using a syringe.

In comparison with the known spherical liposome, the fibrous microtube according to the present invention has much larger inside volume. For example, a fibrous microtube having a diameter of 1 µm and a length of 500 µm has about 800 times as large a volume as a spherical liposome having a diameter of 1 µm. Further, since the spherical vesicles are encapsulated in the tubular body, the retention time of a medicine contained therein can be much increased.

The following examples will further illustrate the present invention. In Examples, Rf1 and Rf2 are Rf values in thin layer chromatography using a chloroform/methanol (5:1 by volume) mixed solvent and a chloroform/methanol/acetic acid (95:5:1 by volume) mixed solvent as developers, respectively.

EXAMPLE 1

Preparation of Glycylglycine Benzyl Ester Hydrochloride

In 80 ml of chloroform were dissolved 14.8 g (42 mmol) of t-butyloxycarbonylglycine-dicyclohexylamine and 14.0 g (41.5 mmol) of glycine benzyl ester p-toluenesulfonic acid salt. To this solution, 70 ml of a chloroform solution containing 8.75 g (45.7 mmol) of 1-ethyl-3-(3-dimethylaminopropyl)carbodiimide hydrochloride (EDAC) were added at −5° C. with stirring. The resulting mixture was stirred for 24 hours. The resulting chloroform solution was successively washed twice with a 10% by weight aqueous citric acid solution, then twice with water, then twice with a 4% by weight aqueous sodium hydrogen carbonate solution and finally twice with water. Thereafter, the organic phase was dried over anhydrous sodium sulfate. The solvent was then completely removed in vacuo to obtain a white oily material. This was crystallized from hexane to obtain 12.8 g (yield: 96%) of t-butyloxycarbonyl-glycylglycine benzyl ester as a white solid. In 10 ml of ethyl acetate were dissolved 8.0 g (24.8 mmol) of t-butyl oxycarbonyl-glycylglycine benzyl ester, to which 120 ml of 4N HCl/ethyl acetate were added. The mixture was stirred for 4 hours and then the solvent was removed in vacuo to obtain white precipitates. The precipitates were washed well with diethyl ether to obtain 6.4 g (yield: 100%) of glycylglycine benzyl ester hydrochloride as a white solid having the following physical properties:

Melting Point: 158–160° C.

Rf1: 0.57

Rf2: 0.05

Preparation of N,N'-Bis(glycylglycine)decane-1,10-dicarboxyamide

In 10 ml of N,N-dimethylformamide (DMF) were dissolved 0.50 g (2.17 mmol) of 1,10-decanedicarboxylic acid and 0.65 g (4.77 mmol) of 1-hydroxybenzotriazole. To this solution, 10 ml of a chloroform solution containing 0.915 g (4.77 mmol) of EDAC were added at −5° C. with stirring and the mixture was stirred for 1 hour at that temperature. To the resulting solution, 10 ml of a methanol solution containing 1.24 g (4.77 mmol) of glycylglycine benzyl ester hydrochloride obtained above, and then 0.67 ml (4.77 mmol) of triethylamine were successively added. The mixture was stirred for 24 hours while gradually increasing the temperature to room temperature. The solvent was then removed in vacuo to obtain white precipitates. The precipitates were washed on a filter paper successively with 50 ml of a 10% by weight aqueous citric acid solution, 20 ml of water, 50 ml of a 4% by weight aqueous sodium hydrogen carbonate solution and 20 ml of water and then crystallized from DMF to obtain 1.15 g (yield: 83%) of N,N -bis(glycylglycine benzyl ester)decane-1,10-dicarboxyamide. This dicarboxyamide (0.5 g (0.78 mmol)) was dissolved in 200 ml of DMF in a water bath at 50° C., to which 0.25 g of a supported catalyst (10% by weight palladium on carbon) was added. The mixture was then subjected to catalytic hydrogenation reduction for 6 hours. After the reaction, the catalyst was removed by filtration with celite and the solvent was distilled under reduced pressure to leave white precipitates. The precipitates were recrystallized from DMF to obtain 14 g (yield: 39%) of N,N'-bis(glycylglycine)-decane-1,10-dicarboxyamide as a white solid having the following physical properties:

Melting point: decomposition at>220° C.

Elementary analysis:

|  | C | H | N |
| --- | --- | --- | --- |
| Calculated (%) | 52.38 | 7.47 | 12.22 |
| Found (%) | 52.40 | 7.46 | 12.11 |

$^1$H-NMR: as shown in FIG. 2 (in dimethylsulfoxide-$d_6$)

EXAMPLE 2

Preparation of Fibrous Microtubes

N,N'-bis(glycylglycine)-decane-1,10-dicarboxyamide (45.9 mg (0.1 mmol)) obtained in Example 1 was mixed with 10 ml of distilled water containing 8 mg (0.2 mmol) of sodium hydroxide and the mixture was sonicated to obtain a solution. This was allowed to quiescently stand at room temperature in air for 3 weeks, thereby forming molecular assemblies in the form of fibrous microtubes having a length of about 300 µm to about 2 mm. Video-enhanced dark field microscopy revealed that, as shown in FIG. 1, each of the fibrous microtubes includes a tubular body which has closed at both ends and in which a plurality of spherical vesicles with a diameter of 1–3 µm are encapsulated. The supernatant was removed by decantation and the precipitates were dehydrated and completely dried in a high vacuum. The fibrous microtubes thus isolated were found to be stable in air.

EXAMPLE 3

The dry fibrous microtubes (10 mg) obtained in Example 2 was mixed with 5 ml of water and the mixture was sonicated to obtain hydrated fibrous microtubes. The phase-contrast microscopy revealed that most of the ends of the microtubes were open to the aqueous medium. The supernatant was removed by decantation and the precipitates were dehydrated and completely dried again in a high vacuum. The fibrous microtubes thus isolated were found to be stable in air.

EXAMPLE 4

Preparation of Glycylglycylglycine Benzyl Ester Hydrochloride

In 380 ml of a chloroform/methylene chloride/ethyl acetate (7:5:1 by volume) mixed solvent were dissolved 7.13 g (20 mmol) of t-butyloxycarbonylglycine. dicyclohexylamine and 5.18 g (20 mmol) of glycylglycine benzyl ester hydrochloride obtained in Example 1. To this solution, 50 ml of a chloroform solution containing 4.22 g (20 mmol) of EDAC were added at −5° C. with stirring. The resulting mixture was stirred for 24 hours. The resulting chloroform solution was successively washed twice with a 10% by weight aqueous citric acid solution, then twice with water, then twice with a 4% by weight aqueous sodium hydrogen carbonate solution and finally twice with water. Thereafter, the organic phase was dried over anhydrous sodium sulfate. The solvent was then completely removed in vacuo to obtain a white oily material. This was crystallized from hexane to obtain 6.52 g (yield: 86%) of t-butyloxycarbonyl-glycylglycylglycine benzyl ester as a white solid. This benzyl ester was dispersed, to which 130 ml of 4N HCl/ethyl acetate were added. The mixture was stirred for 4 hours and then the solvent was removed in vacuo to obtain white precipitates. The precipitates were washed well with diethyl ether to obtain 4.63 g (yield: 85%) of glycylglycylglycine benzyl ester hydrochloride as a white solid having the following physical properties:

Melting Point: 190–193° C.

Rf1: 0.25

Rf2: 0.63

Preparation of N,N'-Bis(glycylglycylglycine)decane-1,10-dicarboxyamide

Using the glycylglycylglycine benzyl ester hydrochloride obtained above, N,N'-bis(glycyl-glycylglycine)decane-1,10-dicarboxyamide was prepared in the same manner as that in the preparation of N,N'-bis(glycyl -glycine)decane-1,10-dicarboxyamide in Example 1.

EXAMPLE 5

Preparation of Fibrous Microtubes

N,N'-bis(glycylglycylglycine)-decane-1,10-dicarboxyamide (57.3 mg (0.1 mmol)) obtained in Example 4 was mixed with 10 ml of distilled water containing 8 mg (0.2 mmol) of sodium hydroxide and the mixture was sonicated to obtain a solution. This was allowed to quiescently stand at room temperature in air for 3 weeks. The supernatant was removed by decantation and the precipitates were dehydrated and completely dried in a high vacuum to obtain fibrous microtubes. The phase contrast microscopy revealed that, as shown in FIG. 1, each of the fibrous microtubes includes a tubular body which has closed at both ends and in which a plurality of spherical vesicles with a diameter of 1–3 µm are encapsulated.

EXAMPLE 6

Preparation of N,N'-Bis(glycylglycylglycine)hexane-1,6-dicarboxyamide

In the same manner as described in Example 4 except that 1,6-hexanedicarboxylic acid was substituted for 1,10-decanedicarboxylic acid, N,N'-bis(glycylglycyl -glycine)

hexane-1,6-dicarboxyamide was prepared using glycylglycylglycine benzyl ester hydrochloride.

EXAMPLE 7
Preparation of Fibrous Microtubes

N,N'-bis(glycylglycylglycine)-hexane-1,6-dicarboxyamide (51.7 mg (0.1 mmol)) obtained in Example 6 was mixed with 10 ml of distilled water containing 8 mg (0.2 mmol) of sodium hydroxide and the mixture was sonicated to obtain a solution. This was allowed to quiescently stand at room temperature in air for 3 weeks. The supernatant was removed by decantation and the precipitates were dehydrated and completely dried in a high vacuum to obtain fibrous microtubes. The phase-contrast microscopy revealed that, as shown in FIG. 1, each of the fibrous microtubes includes a tubular body which has closed at both ends and in which a plurality of spherical vesicles with a diameter of 1–3 µm are encapsulated.

EXAMPLE 8
Preparation of N,N'-Bis (glycylglycylglycine)octadecane-1,18-dicarboxyamide In the same manner as described in Example 4 except that 1,18-octadecanedicarboxylic acid was substituted for 1,10-decanedicarboxylic acid, N,N'-bis(glycylglycylcyl -glycine) octadecane-1,18-dicarboxyamide was prepared using glycylglycylglycine benzyl ester hydrochloride.

EXAMPLE 9
Preparation of Fibrous Microtubes

N,N'-bis(glycylglycylglycine)-octadecane-1,18-dicarboxyamide (68.4 mg (0.1 mmol)) obtained in Example 8 was mixed with 10 ml of distilled water containing 8 mg (0.2 mmol) of sodium hydroxide and the mixture was sonicated to obtain a solution. This was allowed to quiescently stand at room temperature in air for 3 weeks. The supernatant was removed by decantation and the precipitates were dehydrated and completely dried in a high vacuum to obtain fibrous microtubes. The phase-contrast microscopy revealed that, as shown in FIG. 1, each of the fibrous microtubes includes a tubular body which has closed at both ends and in which a plurality of spherical vesicles with a diameter of 1–3 µm are confined.

EXAMPLE 10
Preparation of N,N'-Bis(glycylglycine)hexane-1,6-dicarboxyamide

In the same manner as described in Example 1 except that 1,6-hexanedicarboxylic acid was substituted for 1,10-decanedicarboxylic acid, N,N'-bis(glycylglycine)hexane-1,6-dicarboxyamide was prepared using glycylglycine benzyl ester hydrochloride.

EXAMPLE 11
Preparation of Fibrous Microtubes

N,N'-bis(glycylglycine)-hexane-1,6-dicarboxyamide (40.2 mg (0.1 mmol)) obtained in Example 6 was mixed with 10 ml of distilled water containing 8 mg (0.2 mmol) of sodium hydroxide and the mixture was sonicated to obtain a solution. This was allowed to quiescently stand at room temperature in air for 3 weeks. The supernatant was removed by decantation and the precipitates were dehydrated and completely dried in a high vacuum to obtain fibrous microtubes. The phase-contrast microscopy revealed that, as shown in FIG. 1, each of the fibrous microtubes includes a tubular body which has closed at both ends and in which a plurality of spherical vesicles with a diameter of 1–3 µm are encapsulated.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A process for the preparation of a fibrous microtube comprising a tubular body and a plurality of spherical vesicles contained within said tubular body, each of said tubular body and said vesicles being a lipid represented by the following formula:

$$MO-(CO-CH_2-NH)_p-CO-(CH_2)_n-CO-(NH-CH_2-CO)_q-OM$$

wherein M represents an alkali metal, n is an integer of 6–18 and p and q each represent an integer of at least 1 with the proviso that a total of p and q is not greater than 6, said process comprising the step of allowing an aqueous solution of said lipid to stand in air or in an atmosphere of an organic acid for a period of time sufficient to grow molecular assemblies of said fibrous microtube.

2. A process as claimed in claim 1, further comprising the steps of recovering said molecular assemblies, dehydrating said molecular assemblies, and dissolving said dehydrated molecular assesmblies in water.

3. A process as claimed in claim 1, wherein said allowing step is performed at a temperature of 5–40° C.

* * * * *